US00PP33546P2

(12) United States Plant Patent
Goffreda et al.

(10) Patent No.: US PP33,546 P2
(45) Date of Patent: Oct. 12, 2021

(54) APPLE TREE NAMED NJ150

(50) Latin Name: ***Malus* x *domestica* Borkh**
Varietal Denomination: NJ150

(71) Applicant: RUTGERS, THE STATE UNIVERSITY OF NEW JERSEY, New Brunswick, NJ (US)

(72) Inventors: Joseph C. Goffreda, Columbus, NJ (US); Anna M. Voordeckers, East Windsor, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 17/091,022

(22) Filed: Nov. 6, 2020

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./156, 161
See application file for complete search history.

*Primary Examiner* — Susan McCormick Ewoldt
*Assistant Examiner* — Karen M Redden
(74) *Attorney, Agent, or Firm* — Patrick J. Daugherty; Daugherty & Del Zoppo Co. LPA

(57) ABSTRACT

A new and distinct apple variety of *Malus* x *domestica* Borkh. named 'NJ150' is provided. This variety is distinguished from other apple varieties by its unique combination of excellent production large, high quality aromatic fruit with an attractive red (RHS 53A) blush over a yellow (RHS 11C) ground color on trees that are highly tolerant to cedar apple rust (*Gymnosporangium juniperiviriginianae*) and apple scab (*Venturia inaequalis*) and have low susceptibility to fire blight.

4 Drawing Sheets

STATEMENT REGARDING FEDERALLY SPONSORED RESEARCH OR DEVELOPMENT

This invention was made with government support under contract or grant Multistate Research Project NE-9, entitled "Conservation and Utilization of Plant Genetic Resources," awarded or sponsored by the National Institute of Food and Agriculture. The government has certain rights in the invention.

Latin name of genus and species of the plant claimed: *Malus* x *domestica* Borkh.

Variety denomination: 'NJ150'.

BACKGROUND OF THE INVENTION

The present invention relates to a new and distinct variety of apple tree named 'NJ150' that resulted from crossing 'Co-op 38' (also known as 'Goldrush', U.S. Plant Pat. No. 9,392) as the seed parent with 'Co-op 30' (also known as 'Enterprise', U.S. Plant Pat. No. 9,193) as the pollen parent. The resulting tree was selected when growing in a cultivated area as the 206$^{th}$ tree in the 18$^{th}$ row of Block DW at a fruit research farm in Cream Ridge, N.J.

BRIEF SUMMARY OF THE INVENTION

The 'NJ150' variety is distinguished from 'Co-op 38' (also known as 'Goldrush', U.S. Plant Pat. No. 9,392) in that the new variety has more tolerance to cedar apple rust (*Gymnosporangium juniperiviriginianae*), ripens about one month earlier, and produces fruit that have a better finish and color. The new variety differs from 'Co-op 30' (also known as 'Enterprise', U.S. Plant Pat. No. 9,193) in that the ripens about one week earlier, and produces larger fruit that have a brighter overcolor and better fruit texture and flavor.

Trees are highly tolerant to cedar apple rust (*Gymnosporangium juniperiviriginianae*) and apple scab (*Venturia inaequalis*) and have low susceptibility to fire blight.

Excellent production of large fruit that ripen in mid-late season.

Fruit have superior eating quality due to their aromatic, sweet, and mild acidic flavor.

The variety was asexually reproduced at a fruit research farm in Cream Ridge, N.J. Asexual reproduction of this new variety by budding onto 'EMLA 7' rootstock (non-patented) shows that the foregoing characteristics are so reproduced.

The following detailed description concerns the original tree, 'NJ150'. The original tree and asexual progeny have been observed growing in a cultivated area at a fruit research farm in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions unless the context clearly indicates otherwise. Color designations are made with reference to *The Royal Horticultural Society* (*R.H.S.*) *Colour Chart* (1966 Ed.)

BRIEF DESCRIPTION OF THE DRAWINGS

This new variety is illustrated by the accompanying photographic drawings of the 'NJ150' plant at approximately 4 years old, depicting the apple tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
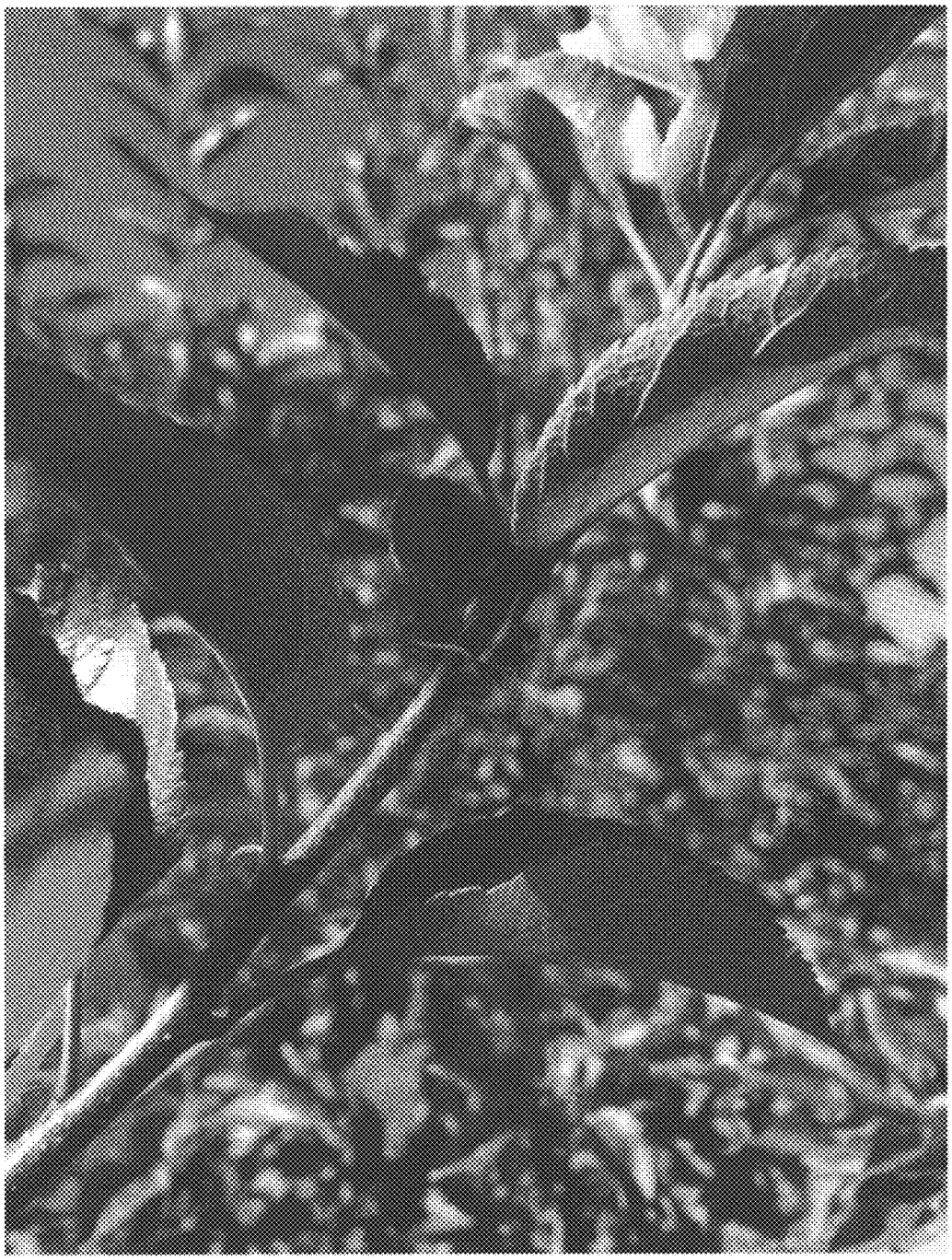
FIG. 1 is a color photograph taken on Oct. 16, 2019, of a characteristic twig of 'NJ150' bearing typical leaves of the foliage.
Figure 2:
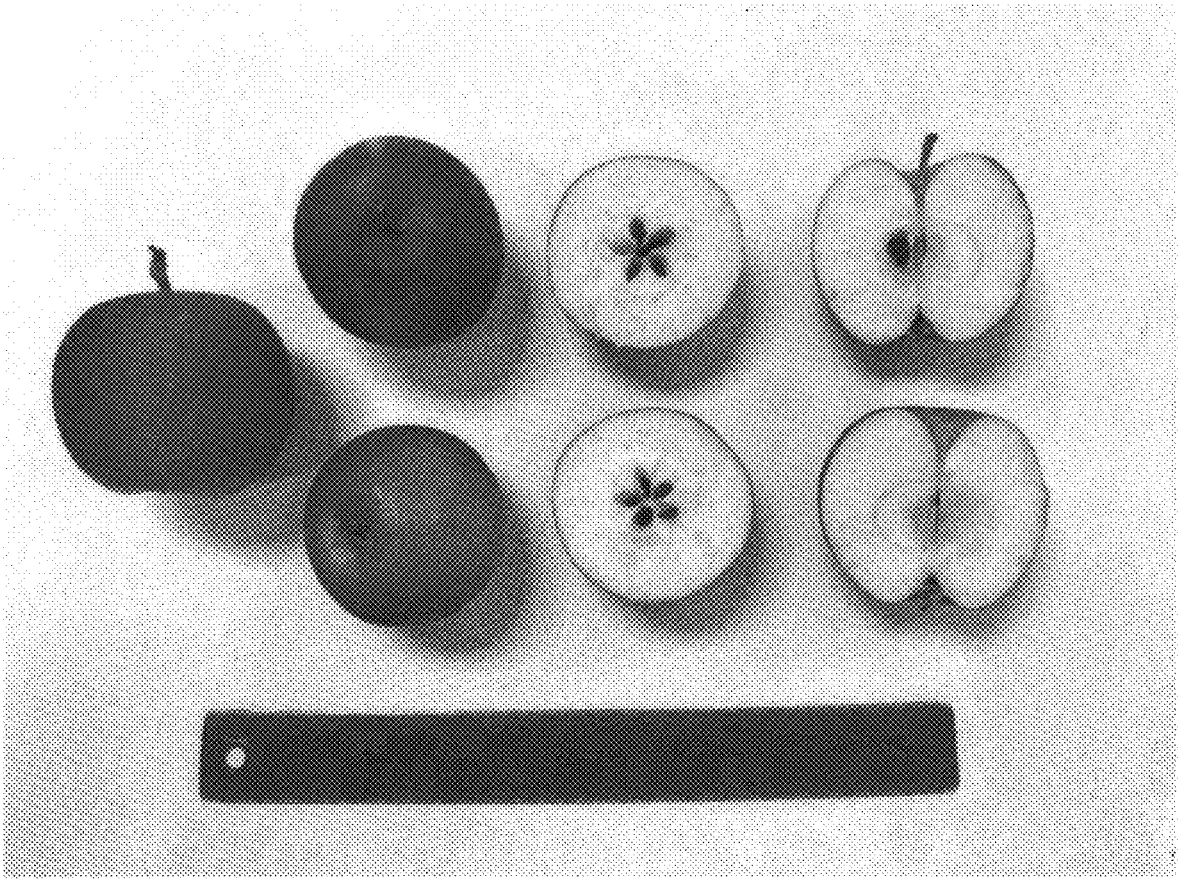
FIG. 2 is a color photograph taken on Oct. 19, 2020, of characteristic mature fruit of 'NJ150'. Whole fruits are presented in three positions and both a transverse and longitudinal cross section to illustrate their globose shape, flaring cavity and persistent sepals with erect tips.
Figure 3:
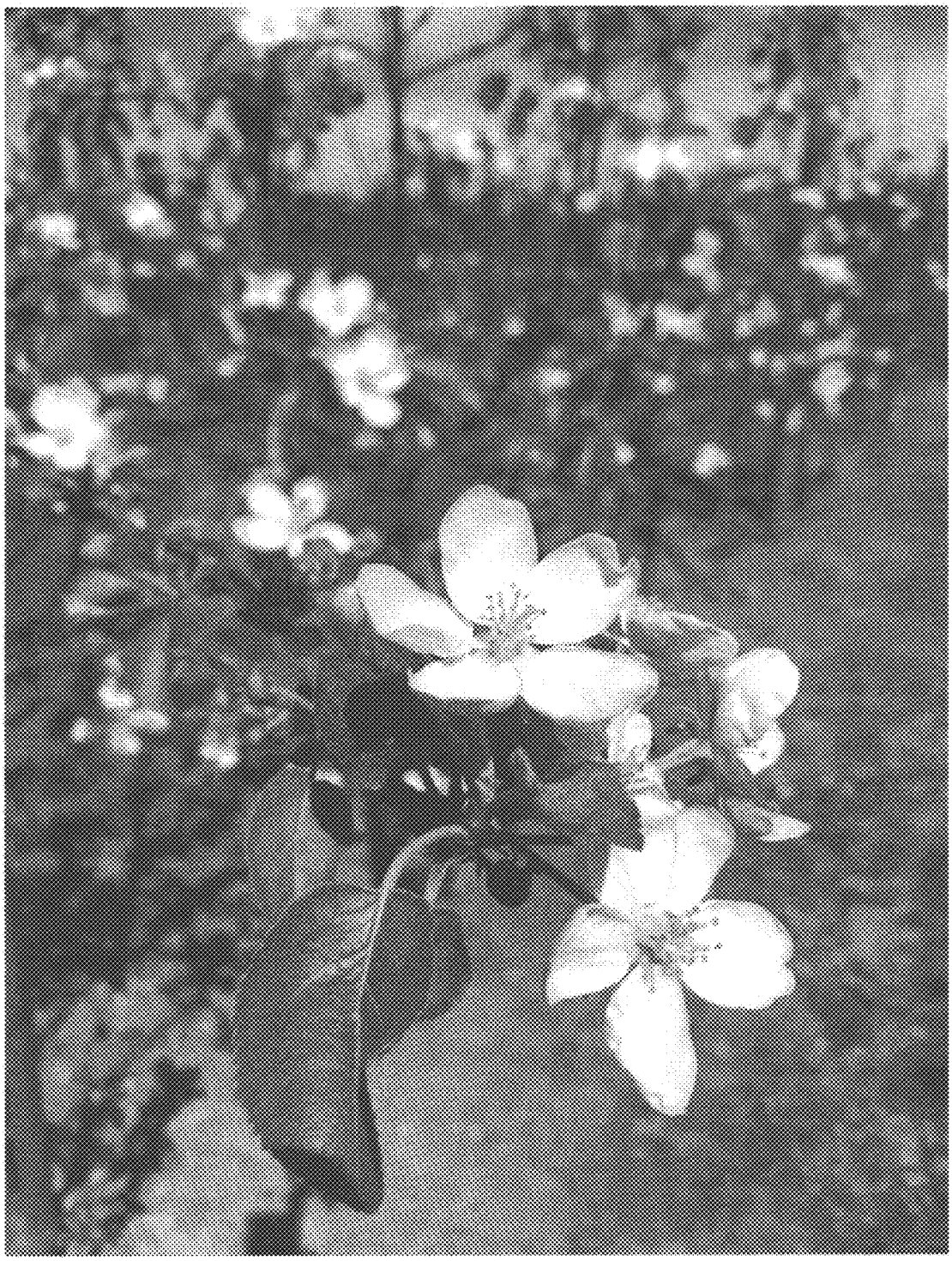
FIG. 3 is a color photograph of a characteristic twig that illustrates the typical open flowers and flower buds of 'NJ150' observed on a tree at a fruit research farm in in Adams County, Pa. on Apr. 22, 2019.
Figure 4:
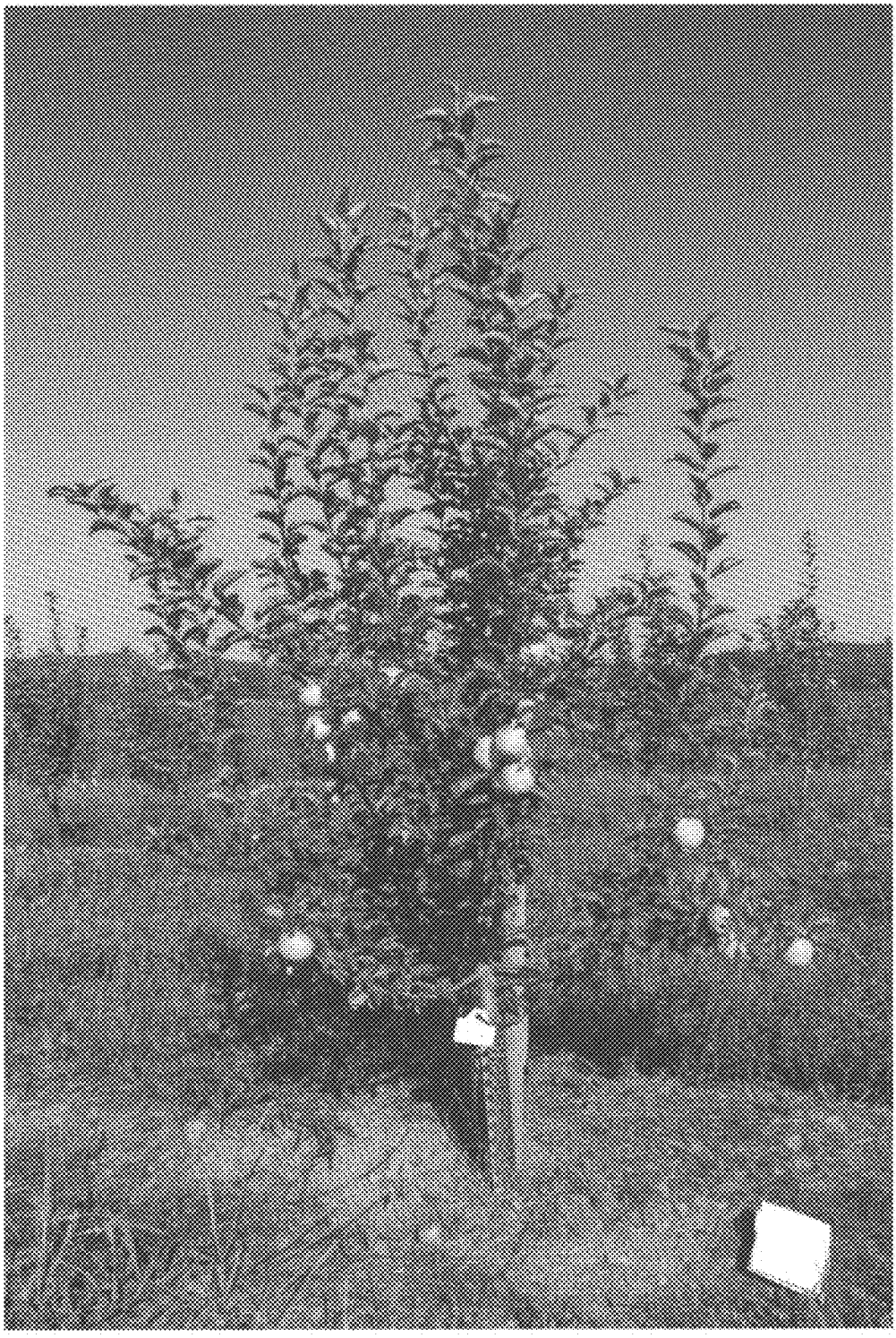
FIG. 4 is a color photograph of a tree of 'NJ150', in mid-summer that illustrates the upright growth habit of a tree at the fruit research farm in in Adams County, Pa. on Aug. 28, 2019.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJ150' variety is based on observations of an asexually reproduced tree. The observed tree was 4 years of age and growing on 'M9/Nic 29' rootstock (non-patented) at the fruit research farm in Adams County, Pa.

Scientific name: *Malus* x *domestica* Borkh.

Parentage:

*Seed parent*.—'Co-op 38'.

*Pollen parent*.—'Co-op 30'.

Tree:

*Vigor*.—Strong.

*Plant hardiness zone*.—Growth of plants has been observed in zone 6b.

*Dormant flower bud cold tolerance*.—At least to −17° C.

*Overall shape*.—Ramified, upright-spreading.

*Height*.—Moderate as compared to other apple trees on 'M9/NIC 29' rootstock.

*Width*.—Moderate as compared to other apple trees on 'M9/NIC 29' rootstock.

Trunk and branches:

*Trunk bark color*.—Greyed-brown (RHS 199A).

*Primary branches*.—Branches are 15 mm in diameter, having about 70 to 80-degree crotch angles, and grey-orange (RHS 165A) in color.

*Branch angle*.—Typically about 70 to 80 degrees.

*Lenticels*.—Approximately 10-12 per $cm^2$, slightly raised, approximately 1 mm long, greyed-orange (RHS 163D) in color. The number of lenticels on a one-year-old shoot is approximately 5-8 per $cm^2$.

*Terminal shoots*.—Average length is approximately 30 cm. The length of the internode of a one-year-old shoot is approximately 1 inch.

*New growth bark*.—Grey-orange (RHS 165B) in color.

Leaves:

*Texture*.—Upper surface leathery; lower surface slightly velvety.

*Length*.—8 cm.

*Width*.—Typically between 4 and 4.5 cm, folding upward.

*Apex*.—Slight cuspidate with pointed bottom, medium thick.

*Venation*.—Reticulate pattern.

*Margin*.—Fine, bi-serrate.

*Petioles*.—Generally, between 1.5 and 2 cm long, and about 2 mm in diameter at the mid-section. Color is red (RHS 53B).

*Stipules*.—Two, with an average length of 7 mm. Color is green (RHS 137A).

Leaf color:

*Upper leaf surface*.—Green (RHS 137A).

*Lower leaf surface*.—Yellow-green (RHS 147B).

*Vein*.—Yellow-green (RHS 145C).

Flowers:

*Size*.—Corolla diameter averaging about 3.8 cm.

*Petals*.—Typically five, ovate shape, soft texture. Length 1.9 cm, width 1.27 cm, and arrangement of single, imbricated (regularly arranged single-life).

*Pistil*.—Length 1.9 cm, color: light yellow green (RHS 1B).

*Stigma color*.—Light yellow green (RHS 1B).

*Stamens*.—Number many, 10+; length: 1 cm; color: white (RHS 155D).

*Pollen*.—Color: Brilliant Yellow (RHS 11A); abundance: medium.

*Flower sepals*.—Length: 1 cm; width: 1 mm; color: green (RHS 138C) ; description: curl back when bud opens.

*Flower calyx shape*.—Spurred.

*Color*.—Dormant bud is red-purple (RHS 60D) , young flower buds are red-purple (RHS 68B) , balloons are red-purple (RHS 68D). Open flowers are white (RHS 155D).

*Pedicel length*.—Average 2.5 cm.

*Bloom season*.—Mid-season. Onset of first and full bloom Adams County, Pa. in 2019 was April 20; full bloom on April 25. Should be pollinated by other mid-season bloom apple varieties.

Fruit:

*Size*.—Uniformly large, averaging 8.9 cm. in diameter, and between 7.6 and 8.9 cm. high.

*Shape*.—Globose.

*Color*.—Overcolor is red (RHS 53A) in color generally as a blush with some striping; ground color is yellow (RHS 11C).

*General color effect*.—Bright crimson red (RHS 57A) over yellow (RHS 11C) background with gold (RHS 20C) stem cavity.

*Skin*.—Thickness: 0.25 mm; medium cuticle wax, slightly rough, with a rough finish.

*Stem*.—Color is greyed-orange, (RHS 175C), lightly pubescent, length medium, between 1 to 2 cm, and 3 mm in diameter.

*Cavity*.—Flaring, depth 1.3 cm., breadth between 1.9-2.5 cm. Color greyed-orange (RHS 163C).

*Basin*.—Depth between 1.4 and 1.6 cm.; breadth 2.5 cm.

*Calyx*.—Sepals persistent with erect tips, mostly closed, diameter 1 cm.

*Calyx tube*.—Cone-shaped.

*Lenticels*.—Small to medium size, moderate number, greyed-orange (RHS 163D).

*Russet*.—Slight, mainly around cavity, greyed-orange, (RHS 163B).

Fruit properties:

*Flesh color*.—Orange-white (RHS 159D).

*Juice*.—Above average.

*Firmness*.—Firm.

*Texture*.—Crisp and breaking.

*Flavor*.—Sweet and mildly acidic.

*Soluble solids*.—14.8%.

*Aroma*.—Highly aromatic.

*Eating quality*.—Very good.

*Keeping quality*.—Best before 4-5 months of storage, yet still highly acceptable after 5 months.

*Harvest date*.—Approximately September 22 in Aspers, Adams County, Pa.

*Productivity of the fruit*.—1,000 lbs. per acre, at an estimate of 42 lbs. per bushel. Due to the nature of the disease resistance of this variety, the crisp and juicy texture, and the storability, the fruit would suit both the commercial and direct markets as well as the possibility of organic markets.

*Core*.—Median position; open, 3 cm. in diameter.

*Core lines*.—Basil, clasping.

*Carpellary area*.—Visible.

*Depth of calyx tube*.—11 mm.

*Seed cells*.—Generally 2 seeds per cell, closed, 5 in number.

*Cell walls*.—Thick, obovate in cross-section; length 1.3 cm, breadth 0.8 cm.

Seeds:

*Number*.—Usually 10.

*Length*.—1 cm.

*Breadth*.—0.5 cm.

*Form*.—Acute.

*Color*.—Greyed-orange (RHS 166A).

*Plant/fruit disease and pest resistance/susceptibility*.—Highly tolerant to apple scab (*Venturia inaequalis*) and cedar apple rust (*Gymnosporangium juniperi-viriginianae*) and has low susceptibility to fire blight. No atypical susceptibilities have been noted under normal cultural practices.

We claim:

1. A new and distinct variety of apple tree 'NJ150', substantially as herein shown and described.

* * * * *